United States Patent
Oshima et al.

(10) Patent No.: US 7,719,673 B2
(45) Date of Patent: May 18, 2010

(54) DEFECT INSPECTING DEVICE FOR SAMPLE SURFACE AND DEFECT DETECTION METHOD THEREFOR

(75) Inventors: Yoshimasa Oshima, Yokohama (JP); Toshiyuki Nakao, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 11/940,483

(22) Filed: Nov. 15, 2007

(65) Prior Publication Data
US 2008/0151235 A1 Jun. 26, 2008

(30) Foreign Application Priority Data
Dec. 20, 2008 (JP) ............... 2006-343425

(51) Int. Cl.
*G01N 21/00* (2006.01)
(52) U.S. Cl. ............... 356/237.4; 250/559.41; 250/559.45
(58) Field of Classification Search ... 356/237.2–237.5, 356/239.7, 239.8; 250/559.41, 559.45; 348/126, 348/128, 130–131; 382/141, 145, 147–149
See application file for complete search history.

(56) References Cited

U.S. PATENT DOCUMENTS

| | | | | |
|---|---|---|---|---|
| 4,668,860 A | * | 5/1987 | Anthon | 250/225 |
| 4,866,264 A | * | 9/1989 | Biricik et al. | 250/225 |
| 5,333,052 A | * | 7/1994 | Finarov | 356/369 |
| 5,764,363 A | * | 6/1998 | Ooki et al. | 356/364 |
| 5,903,342 A | | 5/1999 | Yatsugake et al. | |
| 6,690,469 B1 | | 2/2004 | Shibata et al. | |
| 6,833,913 B1 | | 12/2004 | Wolf et al. | |
| 2001/0030296 A1 | * | 10/2001 | Ishimaru et al. | 250/559.4 |
| 2003/0206299 A1 | * | 11/2003 | Opsal et al. | 356/369 |
| 2005/0094864 A1 | * | 5/2005 | Xu et al. | 382/145 |

FOREIGN PATENT DOCUMENTS

| | | |
|---|---|---|
| EP | 0 335 163 | 10/1989 |
| JP | 01-245136 | 9/1989 |
| JP | 09-304289 | 11/1997 |
| JP | 2000-155099 | 6/2000 |
| JP | 2000-193434 | 7/2000 |
| JP | 2001-343329 | 12/2001 |
| JP | 2005-526239 | 9/2005 |

\* cited by examiner

*Primary Examiner*—Tarifur Chowdhury
*Assistant Examiner*—Michael Lapage
(74) *Attorney, Agent, or Firm*—Antonelli, Terry, Stout & Kraus, LLP.

(57) ABSTRACT

In a defect inspection for a semiconductor substrate, inspection objects include, in addition to a bare Si wafer, a wafer with various films formed on the surface thereof. For a sample formed with a metal film in particular, scattering light generated by surface roughness thereof is large, thus making it difficult to detect a minute defect and a minute foreign substance. It is desirable that a minute defect and a minute foreign substance be detected regardless of scattering light generated by the roughness of the sample surface. Insertion of an analyzer in an optical path of a detection optical system at such an angle that the scattering light generated by the roughness becomes minimum permits suppressing the scattering light generated by the roughness.

15 Claims, 9 Drawing Sheets

DEFECT INSPECTING DEVICE FOR SAMPLE SURFACE AND DEFECT DETECTION METHOD THEREFOR

BACKGROUND OF THE INVENTION

(1) Field of the Invention

The present invention relates to a defect inspection tool and a defect detection method, and more specifically to a foreign substance and defect inspection tool for inspecting a minute foreign substance and a minute defect present on the surface of a semiconductor substrate or the like with high sensitivity and high speed, and a defect detection method.

(2) Description of the Related Arts

In a manufacturing line for a semiconductor substrate, a thin-film substrate, or the like, to maintain and improve the yield ratio of the product, a defect and a foreign substance present on the surface of the semiconductor substrate, the thin-film substrate, or the like are inspected. For example, for a sample such as a semiconductor substrate before circuit pattern formation, it is required to detect a minute defect and foreign substance of 0.05 μm or less in size on the surface. With conventional inspection tools, for example, as in Japanese Patent Application Laid-Open Publication No. H9-304289) and U.S. Pat. No. 5,903,342, to detect such a minute defect and such a minute foreign substance, a laser beam condensed into several tens of micrometers in size is irradiated to a sample surface, and scattering light from the defect and the foreign substance is condensed and detected.

SUMMARY OF THE INVENTION

In a defect inspection for a semiconductor substrate, inspection objects include, in addition to a bare Si wafer, a wafer with various films formed on the surface thereof. For a sample formed with a metal film in particular, scattering light generated by surface roughness thereof is large, thus making it difficult to detect a minute defect and a minute foreign substance.

Therefore, it is an object of the present invention to provide a defect inspection tool and a defect detection method capable of detecting a minute defect and a minute foreign substance regardless of scattering light generated by roughness of a sample surface.

Main configuration of one aspect of the invention includes: a laser light source; an illumination optical system for controlling light emitted from the laser light source; a sample support for holding a sample to be inspected; and a detection optical system for, when light emitted from the illumination optical system is irradiated to a surface of the sample to be inspected, detecting first scattering light scattered from an object including a foreign substance and defect present on the surface and second scattering light scattered from surface roughness the surface has. The detection optical system includes: a condensing part for condensing the first and second scattering light; a photoelectric converter for converting these condensed scattering light into an electrical signal; and an analyzer for suppressing the second scattering light inputted to the photoelectric converter.

Insertion of the analyzer in an optical path of the detection optical system at such an angle that the scattering light generated by the roughness becomes minimum suppresses the scattering light generated by the roughness, thereby permitting detection of a minute defect and a minute foreign substance.

As described above, the invention can achieve an inspection while suppressing scattering light from roughness by the analyzer, thus permitting a detection of a minute foreign substance and a minute defect even in a sample formed with a metal film and large roughness.

BRIEF DESCRIPTION OF THE DRAWINGS

These and other features, objects and advantages of the present invention will become more apparent from the following description when taken in conjunction with the accompanying drawings wherein.

DETAILED DESCRIPTION OF THE PREFERRED EMBODIMENTS

Hereinafter, the embodiments of the present invention will be described with reference to the accompanying drawings.

First Embodiment

Figure 2:
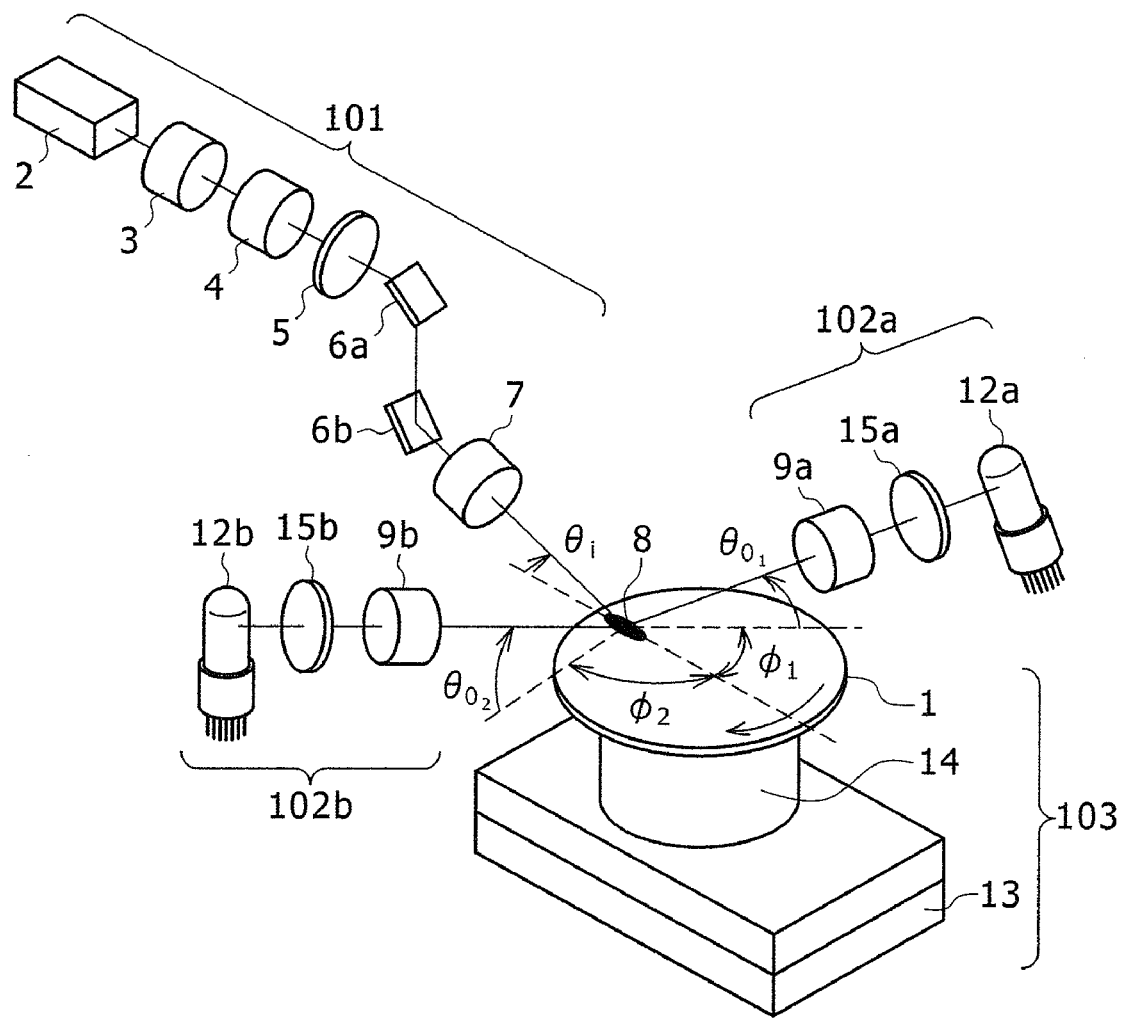
FIG. 2 is a diagram showing another embodiment of the present invention.

FIG. 2 shows one example of a tool for detecting a defect and a foreign substance on a semiconductor wafer according to the invention. FIG. 2 shows a case where a defect and a foreign substance on the semiconductor wafer before circuit pattern formation is detected. As schematic configuration, this tool is composed of an illumination optical system 101, detection optical systems 102, and a wafer stage 103. Two detection optical systems 102a and 102b are shown in FIG. 2. Note that the number of detection optical systems provided may be one or more.

The illumination optical system 101 is composed of a laser light source 2, an attenuator 3, a beam expander 4, a wavelength plate 5, and a condensing lens 7. A laser beam emitted from the laser light source 2 is adjusted to a required light amount by the attenuator 3, the beam diameter is expanded by the beam expander 4, and the polarization direction of illumination is set by the wavelength plate 5 to illuminate a detection area 8 of a wafer 1 while condensing light thereon by the condensing lens 7. Numerals 6a and 6b denote mirrors for changing the illumination optical path, and they are used when necessary. The wavelength plate 5 sets illuminating polarized light to S-polarized light, P-polarized light, or circular polarized light.

The detection optical system 102 is composed of a scattering light detecting lens 9 and a photoelectric conversion element 12. Scattering light from a foreign substance and a defect present in the detection area is condensed on the light receiving surface of the photoelectric conversion element 12 by the scattering light detecting lens 9. The photoelectric conversion element 12 generates an electrical signal of a magnitude proportional to the amount of scattering light received, and a signal processing circuit (not shown) performs signal processing to thereby detect a foreign substance and a defect and then detect the magnitude and position thereof. The photoelectric conversion element 12 is used for receiving this scattering light condensed by the detection optical system 102 and then performing photoelectric conversion thereon. Examples of such a photoelectric conversion element 12 include a TV camera, a COD linear sensor, a TDI sensor, and a photoelectric multiplier tube.

The wafer stage 103 is composed of a chuck (not shown) for holding the wafer 1, a rotating mechanism 14 for rotating the wafer 1, and a straight feed mechanism 13 for feeding the wafer 1 straight in the radial direction. Horizontal rotational scanning and straight movement of the wafer 1 on the wafer stage 103 permits detection of a foreign substance and a defect over the entire region of the wafer 1 and also permits magnitude measurement thereof.

The attenuator 3 is composed of a ½ wavelength plate and a polarized beam splitter (PBS). The attenuator 3 changes, by the ½ wavelength plate, the polarization direction of a beam (linear polarized light) emitted from the laser light source to change the amount of light passing through the PBS. Rotating the ½ wavelength plate changes the polarization direction, thereby permitting adjustment of the amount of light.

The detection optical systems 102 can be oriented multi-directionally, and outputs of photoelectric conversion elements 12a and 12b are subjected to addition, subtraction, division, or the like in accordance with purposes.

When a metal film or the like is formed on the surface of the wafer 1, the photoelectric conversion element 12 receives, in addition to scattering light from a foreign substance and a defect, scattering light from roughness of the sample surface. Thus, an analyzer 15 is inserted in an optical path of the detection optical system 102 and its angle is set so that the scattering light from the roughness becomes minimum. The angle setting is achieved by measuring the scattering light from the roughness, and this angle is fixed after set.

Figure 3:
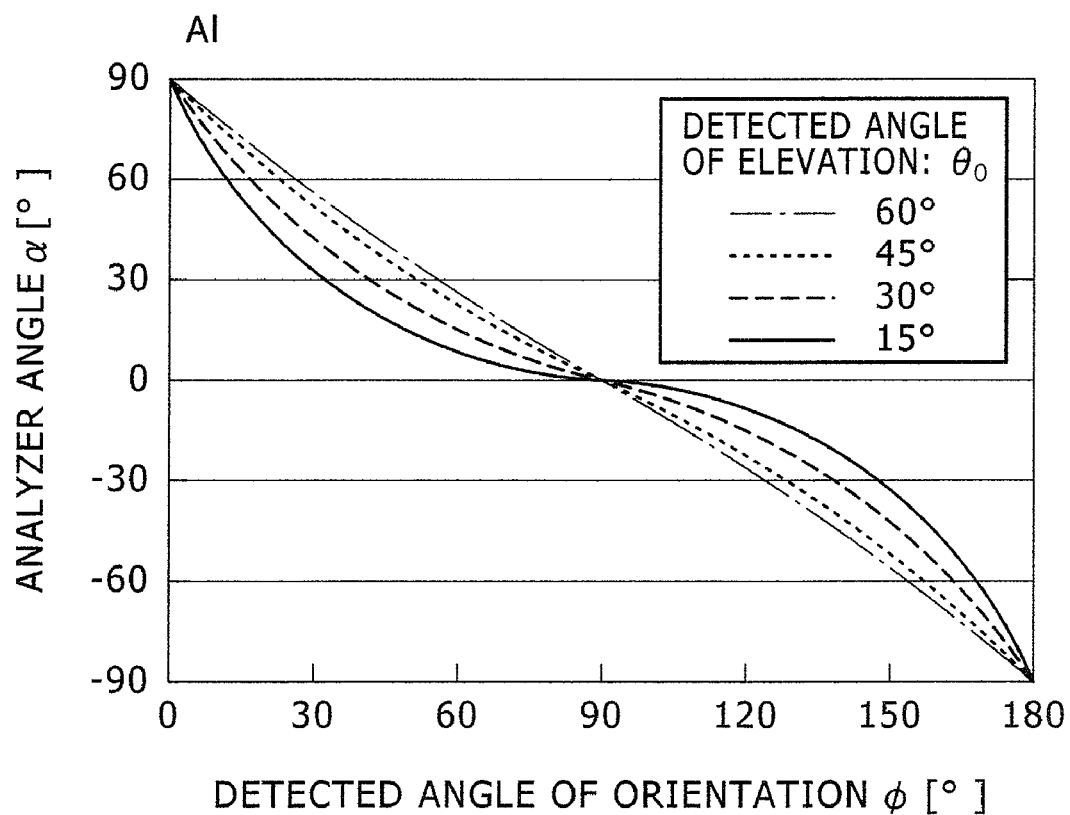
FIG. 3 is a diagram illustrating a relationship between the orientation of a detection optical system and the analyzer angle.

FIG. 3 shows a relationship between the analyzer angle and the detected angle of orientation where the horizontal axis defines a detected angle of orientation $\phi°$, the vertical axis defines an analyzer angle $\alpha°$ at which scattering light from roughness becomes minimum, and a detected angle of elevation $\theta_0$ is changed from 15 degrees to 60 degrees. Here, the detected angle of orientation forms an angle ranging from 0 to 180 degrees clockwise or counterclockwise, with respect to a cross line formed by orthogonal crossing of a plane including the travel direction of light that has passed through the illumination optical system and the surface of the wafer stage. The analyzer angle forms an angle through which the analyzer rotates in the positive or negative direction, with an arbitrarily determined line as an origin. The angle of elevation forms an angle of up to 90 degrees from the surface of the wafer stage as an origin.

As shown in FIG. 3, the analyzer angle varies depending on the detected angle of orientation $\phi°$ and the detected angle of elevation $\theta_0$ of the detection optical system 102. Further, the analyzer angle also varies depending on the polarization direction (S, P, or circular) of illumination.

Figure 4:
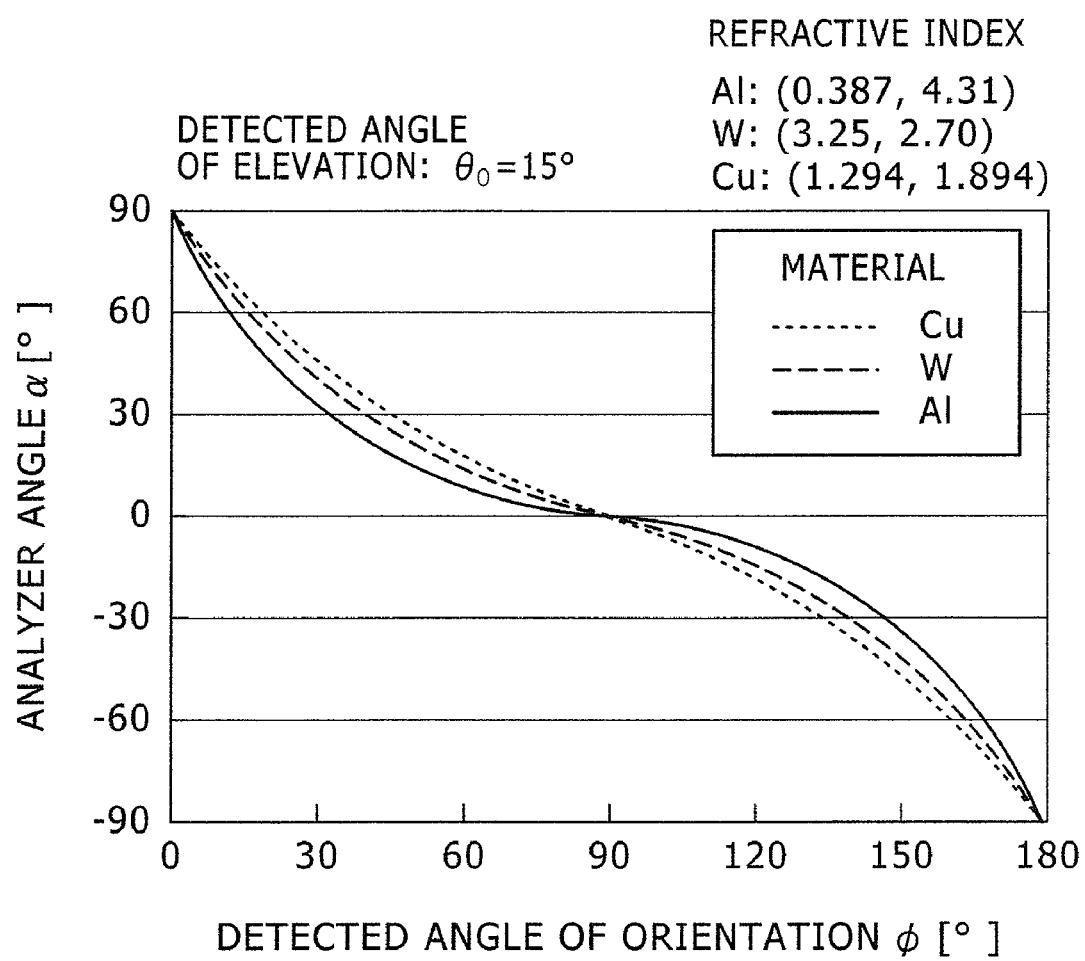
FIG. 4 is a diagram illustrating a relationship between film materials and the analyzer angle.

FIG. 4 is a graph showing the analyzer angle for materials (Cu, W, and Al) of a film formed on the surface of the wafer 1. The vertical and horizontal axes are the same as those in FIG. 3. Illumination condition is as follows: a wavelength of 355 nm, S polarized light, an illumination angle of elevation ($\theta i$) of 20 degrees, and a detected angle of elevation ($\theta o$) of 15 degrees.

Figure 5:
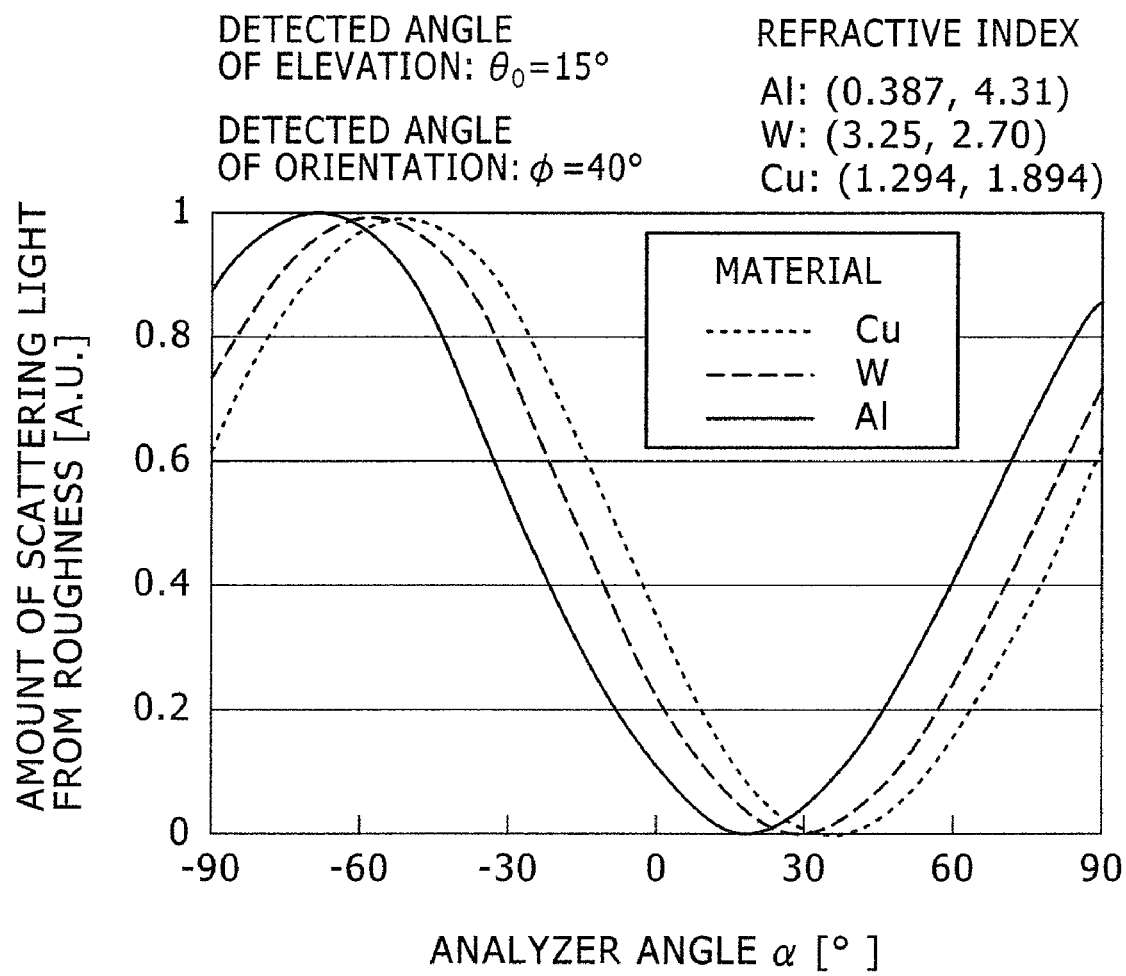
FIG. 5 is a diagram illustrating a relationship between the film materials and the analyzer angle.

FIG. 5 shows the amount of scattering light from roughness at a detected angle of elevation ($\theta_o$) of 15 degrees and a detected angle of orientation ($\phi$) of 40 degrees under the same illumination condition as that of FIG. 4. The horizontal axis denotes the analyzer angle, and the vertical axis denotes the amount of scattering light from roughness, and they are normalized so that a maximum value for each material becomes "1". The values are shown for the film materials Al, W, and Cu, and the analyzer angle at which scattering light from roughness becomes minimum varies depending on a complex refractive index of the film material. As can be understood from FIGS. 4 and 5, the optimum analyzer angle varies depending on the detected angle of elevation ($\theta_0$), the detected angle of orientation ($\phi$), the complex refractive index of the film material, and the illumination condition (illumination angle of elevation $\theta i$ and polarization direction).

Second Embodiment

Figure 1:
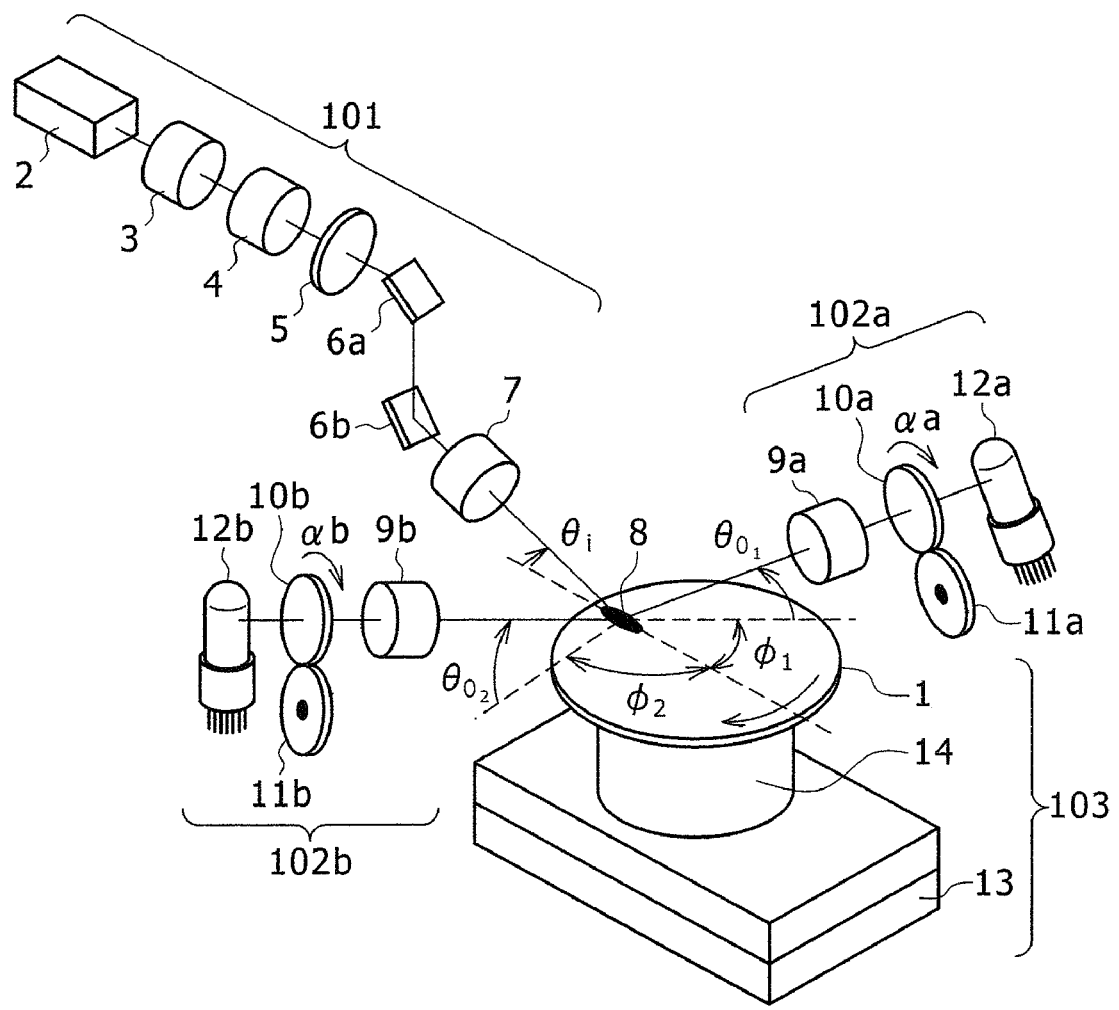
FIG. 1 is a diagram showing one embodiment of the present invention.

As described above, the optimum analyzer angle varies depending on the condition such as the detected angle of elevation ($\theta_0$), the detected angle of orientation ($\phi$), and the like. FIG. 1 shows one embodiment for this case. Tool configuration and an illumination optical system are the same as those of FIG. 2. One or more detection optical systems may be provided, as is the case with that of FIG. 1. An analyzer 10 to be inserted in the detection optical system is configured to be rotatable, and the rotation of the analyzer 10 is controlled by a rotating mechanism 11. This configuration permits constantly inspecting a foreign substance and a defect under optimum detection condition by controlling the angle ($\alpha$) of the analyzer 10 even in a case where the detected angle of elevation ($\theta_0$), the detected angle of orientation ($\phi$), the complex refractive index of the film material, and the illumination condition (illumination angle of elevation $\theta i$ and polarization direction) vary.

Figure 6:
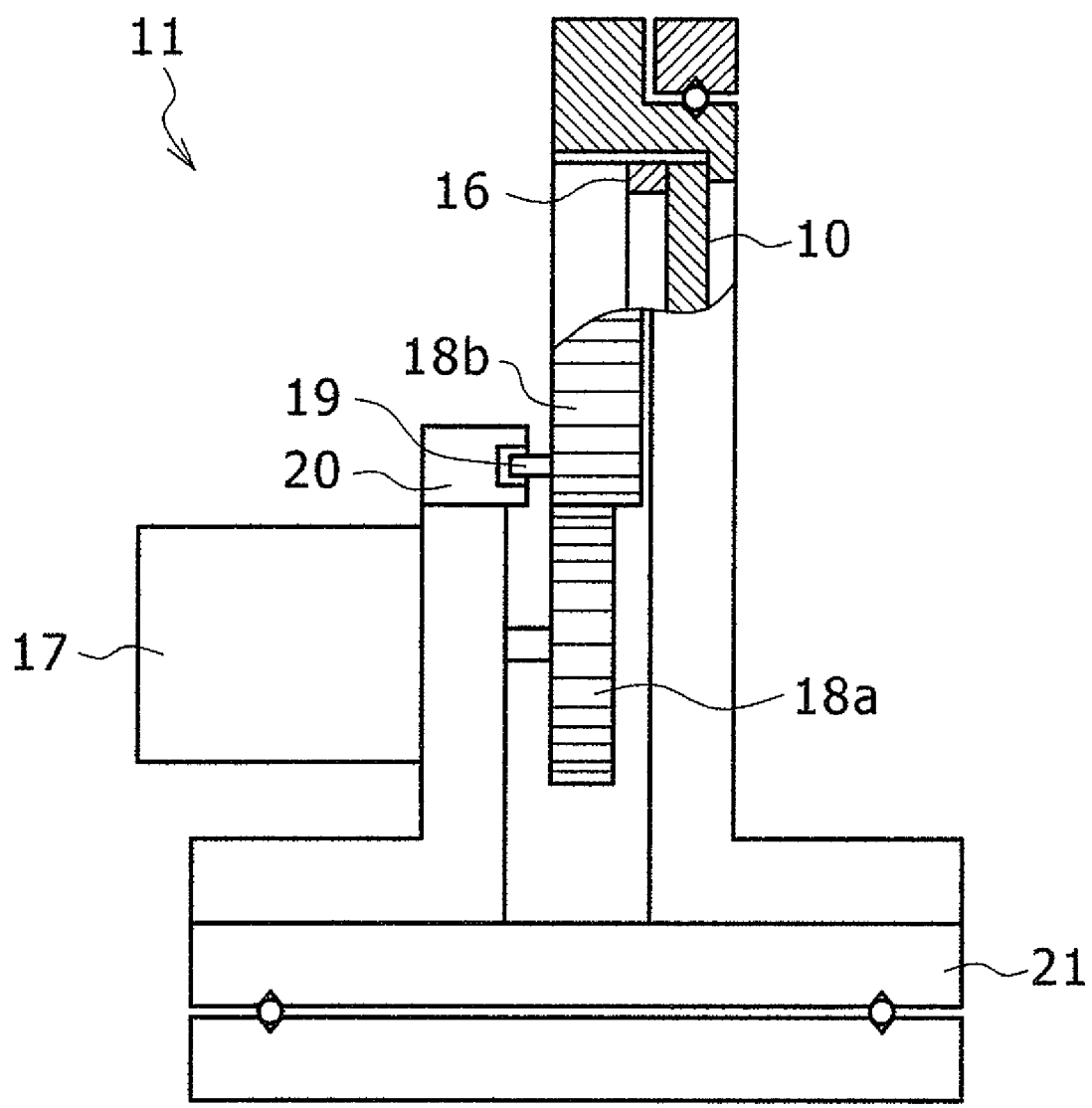
FIG. 6 is a diagram illustrating one embodiment of an analyzer rotating mechanism.

FIG. 6 shows one embodiment of the mechanism 11 for controlling the rotation of the analyzer 10. The analyzer 10 is fixed inside the rotating mechanism with a ring 16. The rotating mechanism is rotated by a pulse motor 17 via gears 18a and 18b. The rotation angle of the analyzer 10 is controlled through calculation of the resolution (the numbers of pulses per rotation) of the pulse motor 17 and the gear ratio between the gears. The origin of the rotating mechanism lies at a point where a cog 19 fitted to the rotating mechanism crosses a photoelectric switch 20. The rotating mechanism 11 is mounted on a linear motion stage 21, and so structured as to be capable of escaping from the optical path under inspection condition where the analyzer 10 is not required. Methods of determining the angle ($\alpha$) of the analyzer 10 are based on:

(1) angle at which the scattering light from the roughness becomes minimum, and (2) angle at which the ratio (S/N) between a defect detection signal and a roughness detection signal becomes maximum.

Figure 7:
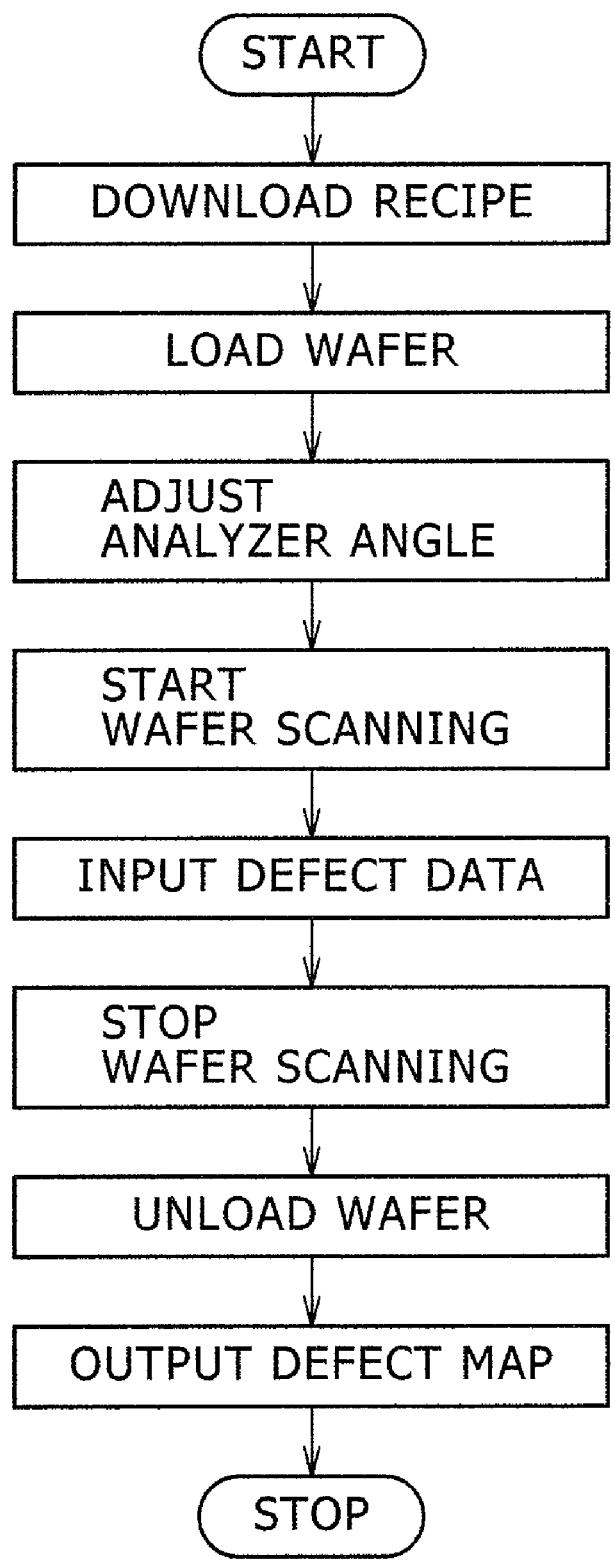
FIG. 7 is a diagram illustrating an inspection flow.
Figure 8:
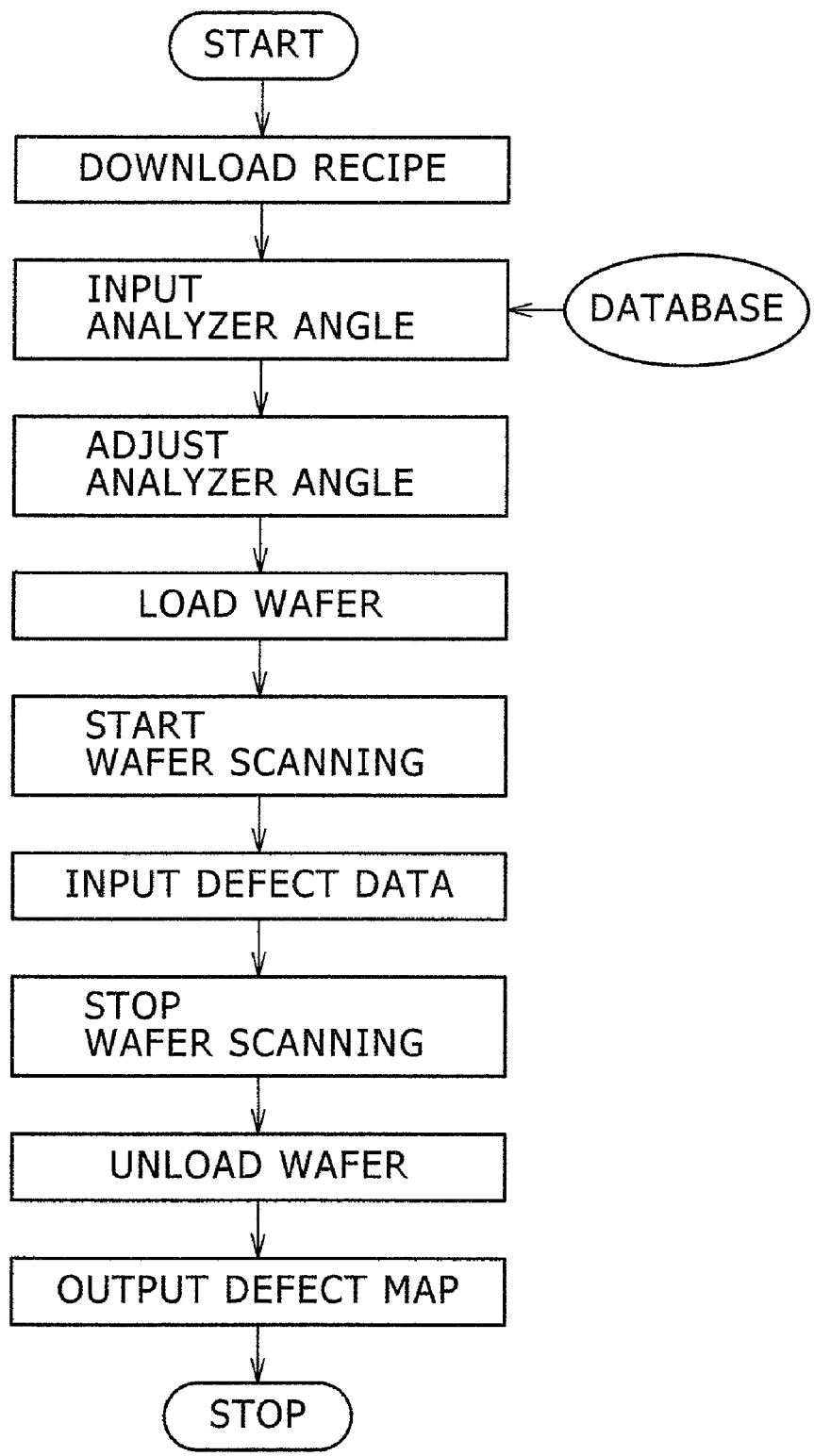
FIG. 8 is a diagram illustrating another inspection flow.

For the case (1) above, as in an inspection flow shown in FIG. 7, after the angle is adjusted so that the roughness signal becomes the minimum at the time when the wafer is loaded, the wafer is inspected. In addition, at the time when a recipe is downloaded, the angle can also be adjusted by calculating the rotation angle based on the inspection condition and the complex refractive index of the film material. In the recipe, the intensity of laser light, the angle of polarization (S, P, and circular), the analyzer angle, and the like are inputted. The angle can also be adjusted by calculating the rotation angle based on the inspection condition, the orientation of the detection optical system 102, and the complex refractive index of the film material, previously preparing a database on rotation angles, and then inputting from the database the analyzer angle that agrees with the inspection condition at the time when the inspection recipe is downloaded. FIG. 8 shows an inspection flow in this condition. In the database, a list of materials and the analyzer in correspondence with each other is inputted.

For the case (2) above, a database based on the inspection condition and the complex refractive indexes of the material can be prepared for each orientation of the detection optical system 102 through actual measurement or calculation, and then the analyzer angle can be adjusted after the recipe is downloaded, as in the inspection flow shown in FIG. 8.

Figure 9:
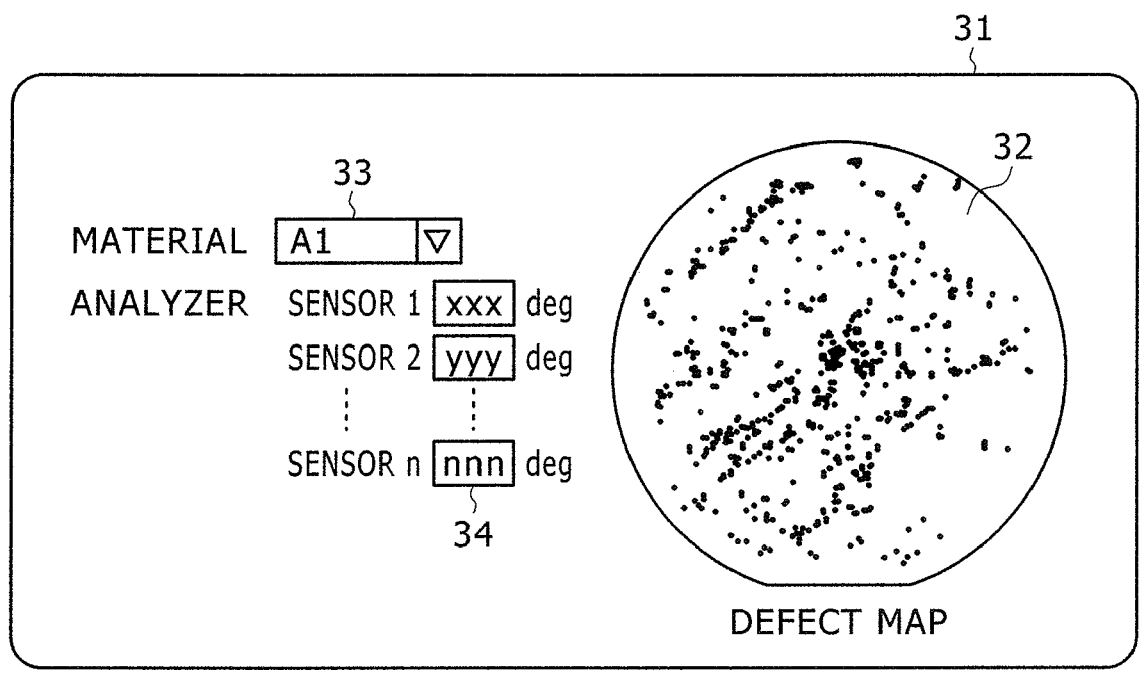
FIG. 9 is a diagram showing one example of a GUI.

FIG. 9 shows one example of a GUI. The GUI screen 31 is essentially composed of: a defect map 32 displayed after an inspection is ended; a sub window 33 for inputting a material before an inspection; and a sub window 34 for displaying an analyzer angle for each detection optical system. The defect map is displayed based on a defect signal and defect position coordinates downloaded at the inspection. Inputting a material can be achieved by either direct inputting or pull-down selection. The sub window 34 for analyzer angle display permits confirmation of the presence or absence of erroneous setting of the analyzer angle.

What is claimed is:

1. A defect inspection device comprising:
   a laser light source;
   an illumination optical system which controls light emitted from the laser light source;
   a sample support which holds a sample to be inspected; and
   a detection optical system which, when light emitted from the illumination optical system is irradiated to a surface of the sample to be
   inspected under an inspection condition, detects first scattering light scattered from an object on a surface of the sample including a foreign substance and a defect present on the surface and second scattering light scattered from surface roughness of the surface of the sample;
   wherein the detection optical system includes:
      a condensing part for condensing the first and second scattering light;
      a photoelectric converter for converting the first and second condensed scattering light into an electrical signal; and
      an analyzer disposed between the condensing part and the photoelectric converter and configured so as to be rotatable about an optical center axis of the detection optical system;
      a storage member which stores a database of analyzer angles in correspondence with inspection conditions including a direction of polarization, a direction of the detection, and a complex refractive index of a film material;
      a retrieval member which retrieves an inspection recipe including the inspection condition for the sample to be inspected; and
      an adjuster which adjusts the angle of the analyzer based upon the inspection recipe and the inspection condition of the sample retrieved by the retrieval member in accordance with the stored database which stores a relationship of each of inspection conditions and the angle of the analyzer stored by the storage member; and
   wherein the defect inspection device, based on the electrical signal at the adjusted angle of the analyzer, detects the foreign substance and the defect present on the surface of the sample to be inspected.

2. The defect inspection device according to claim 1, wherein, as the detection optical system, at least two detection optical systems are provided.

3. The defect inspection device according to claim 1, wherein the illumination optical system has:
   the laser light source;
   an attenuator for adjusting an amount of light emitted from the laser light source;
   a beam expander for expanding a beam diameter of light that has passed through the attenuator; and
   a wavelength plate for setting polarization of light illuminating the sample to be inspected.

4. The defect inspection device according to claim 1, provided with, as the detection optical system, at least two detection optical systems and capable of detection in multiple directions,
   wherein the angle of the analyzer is set for each of the detection directions.

5. The defect inspection device according to claim 1, wherein the angle of the analyzer is set so as to minimize the second scattering light inputted into the photoelectric converter.

6. The defect inspection device according to claim 1, wherein the sample to be inspected is a wafer formed with a metal film.

7. The defect inspection device according to claim 6, wherein the angle of the analyzer is set so that an intensity of the second scattering light becomes a minimum.

8. The defect inspection device according to claim 7, wherein the angle of the analyzer is adjusted after the inspection recipe is retrieved.

9. The defect inspection device according to claim 8, wherein the inspection recipe includes an intensity of laser light and an angle of polarization as the inspection condition.

10. A defect detection method, by using a defect inspection device including:
    a laser light source;
    an illumination optical system for controlling light emitted from the laser light source;
    a sample support for holding a sample to be inspected; and
    a detection optical system for, when light emitted from the illumination optical system is irradiated to a surface of the sample to be inspected under an inspection condition, detects first scattering light scattered from an object on a surface of the sample including a foreign substance and a defect present on the surface and second scattering light scattered from surface roughness of the surface of the sample, the detection optical system having: a condensing part for condensing the first and second scattering light; a photoelectric converter for converting the first and second scattering light into an electrical signal; and an analyzer disposed between the condensing part and the photoelectric converter for suppressing the second scattering light inputted to the photoelectric converter, the analyzer having an adjustable angle;
    a storage member which stores a database of analyzer angles in correspondence with inspection conditions including a direction of polarization, a direction of the detection, and a complex refractive index of a film material; and
    a retrieval member which retrieves an inspection recipe including the inspection conditions for the sample to be inspected
    wherein the defect detection method comprises the step of setting the angle of the analyzer based upon the inspection recipe and the inspection condition of the sample retrieved by the retrieval member in accordance with the stored database which stores a relationship of each of inspection conditions and the angle of the analyzer stored by the storage member so that intensity of the second scattering light becomes a minimum.

11. The defect detection method according to claim 10, wherein the sample to be inspected is a bare Si wafer.

12. The defect detection method according to claim 10, wherein the sample to be inspected is a wafer formed with a metal film.

13. The defect detection method according to claim 10, wherein as the detection optical system, at least two detection optical systems are provided, and wherein the angle of the analyzer is set for each of the detection directions.

14. The defection detection method according to claim 10, wherein the defect detection device, based on the electrical signal at the adjusted angle of the analyzer, detects the foreign substance and the defect present on the surface of the sample.

15. The defect inspection method according to claim 10, wherein the angle of the analyzer is adjusted after the inspection recipe is retrieved.

* * * * *

UNITED STATES PATENT AND TRADEMARK OFFICE
CERTIFICATE OF CORRECTION

| | | |
|---|---|---|
| PATENT NO. | : 7,719,673 B2 | Page 1 of 1 |
| APPLICATION NO. | : 11/940483 | |
| DATED | : May 18, 2010 | |
| INVENTOR(S) | : Oshima et al. | |

It is certified that error appears in the above-identified patent and that said Letters Patent is hereby corrected as shown below:

Title Page, Item (30) should read:

(30) Foreign Application Priority Data

Dec. 20, 2006   (JP) ..............2006-343425

Signed and Sealed this

Ninth Day of November, 2010

David J. Kappos
*Director of the United States Patent and Trademark Office*